United States Patent [19]
Copp et al.

[11]  4,226,876
[45]  Oct. 7, 1980

[54] ARTHROPODICIDAL IMIDAZOLINE DERIVATIVES

[75] Inventors: Frederick C. Copp, Beckenham; Peter T. Roberts, Berkhamsted; Alexander D. Frenkel, Aston Clinton; David Collard, Beckenham, all of England

[73] Assignee: Burroughs Wellcome Co., Research Triangle Park, N.C.

[21] Appl. No.: 968,422

[22] Filed: Dec. 11, 1978

Related U.S. Application Data

[63] Continuation-in-part of Ser. No. 862,168, Dec. 19, 1977, abandoned.

[30] Foreign Application Priority Data

Dec. 20, 1976 [GB] United Kingdom ............... 53059/76
Dec. 20, 1976 [GB] United Kingdom ............... 53061/76
Dec. 20, 1976 [GB] United Kingdom ............... 53062/76
Oct. 26, 1977 [GB] United Kingdom ............... 44485/77
Jun. 19, 1978 [GB] United Kingdom ............... 27295/78

[51] Int. Cl.$^3$ ................ A61K 31/415; C07D 233/22; C07D 233/24
[52] U.S. Cl. ........................... 424/273 R; 260/558 A; 260/558 S; 260/551 S; 260/559 B; 260/559 T; 548/351; 548/353
[58] Field of Search ..................... 548/353; 424/273 R

[56] References Cited

U.S. PATENT DOCUMENTS

| 2,149,473 | 3/1939 | Sonn ........................... 548/353 |
| 3,449,355 | 6/1969 | White .......................... 548/353 |
| 3,996,366 | 12/1976 | Baker et al. ................ 424/273 R |

FOREIGN PATENT DOCUMENTS

| 2260025 | 6/1973 | Fed. Rep. of Germany ........... 548/341 |
| 2454795 | 5/1975 | Fed. Rep. of Germany ........... 548/337 |
| 51-106739 | 9/1976 | Japan ........................ 548/353 |
| 76-1508 | 3/1976 | South Africa ................ 548/353 |
| 1174349 | 12/1969 | United Kingdom .............. 548/353 |
| 1181356 | 2/1970 | United Kingdom .............. 548/353 |
| 1308277 | 2/1973 | United Kingdom .............. 548/351 |
| 1308278 | 2/1973 | United Kingdom .............. 548/351 |
| 1308846 | 3/1973 | United Kingdom .............. 548/351 |
| 1408877 | 10/1975 | United Kingdom .............. 548/341 |

OTHER PUBLICATIONS

Miescher et al., Helv. Chim. Acta 1951, vol. 34, pp. 1–17.
Kaito et al., Chem. Pharm. Bull., Tokyo, 1972, vol. 20, pp. 700–707.

Primary Examiner—John M. Ford
Assistant Examiner—Richard A. Schwartz

Attorney, Agent, or Firm—Donald Brown

[57] ABSTRACT

Compounds of formula (I):

$$Ar-X^1-\underset{R^2}{\underset{|}{\overset{R^1}{\underset{|}{C}}}}-\underset{|}{\overset{N}{\underset{N}{\diagdown}}}\diagup$$

wherein Ar is an unsubstituted or mono-, di or tri-substituted phenyl radical in which the substituents are the same or different and are selected from alkyl, alkoxy, halogen, hydroxy, cyano, amino, trifluoromethyl or nitro and in which any two adjacent carbon atoms on the phenyl ring may optionally be joined by a carbon chain having 3 or 4 carbon atoms;

$X^1$ is O or NH;

$R^1$ and $R^2$ are the same or different and are hydrogen or alkyl; and

Z is a group $SO_nR^8$ or a group $$-C\diagup_{R^3}^{X^2}$$

in which $X^2$ is O, S or $NR^4$;

$R^3$ is alkyl, aryl, alkyloxy, aryloxy or $NR^5R^6$;

$R^4$ is alkyl, aryl, alkyloxy, aryloxy, alkylthio, arylthio or $NR^5R^6$;

$R^5$ and $R^6$ are the same or different and are hydrogen, alkyl, aryl, $COR^7$ or $SO_2R^7$;

$R^7$ is alkyl, aryl, alkoxy or aryloxy;

$n$ is 1 or 2;

$R^8$ is alkyl, aryl or $NR^9R^{10}$; and $R^9$ and $R^{10}$ are the same or different and are hydrogen, alkyl or aryl, provided that when Ar is unsubstituted phenyl, $X^1$ is NH, $R^1$ and $R^2$ are H, Z is $$-C\diagup_{R^3}^{X^2}$$

and $X^2$ is O, $R^3$ is not methyl, methods of making such compounds, pesticidal formulations containing them and their use as pesticides are disclosed.

60 Claims, No Drawings

ARTHROPODICIDAL IMIDAZOLINE DERIVATIVES

EARLIER APPLICATION

This is a continuation-in-part of U.S. Pat. application Ser. No. 862,168 filed Dec. 19, 1977 now abandoned.

This invention relates to imidazolines, their preparation and intermediates therefor, pesticidal formulations containing the imidazolines, and to their use as pesticides.

We have discovered that the compounds of formula (I) below and their acid addition salts have activity against Arthropods, in particular against members of the Order Acarina.

Compounds of formula (I) are:

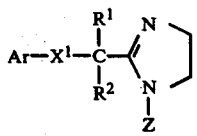

(I)

wherein Ar is an unsubstituted or mono-, di- or tri-substituted phenyl radical in which the substituents are the same or different and are selected from alkyl, alkoxy, halogen, hydroxy, cyano, amino, trifluoromethyl or nitro and in which any two adjacent carbon atoms on the phenyl ring may optionally be joined by a carbon chain having 3 or 4 carbon atoms;

$X^1$ is O or NH;

$R^1$ and $R^2$ are the same or different and are hydrogen or alkyl; and

Z is a group $SO_nR^8$ or a group

in which $X^2$ is O, S or $NR^4$;

$R^3$ is alkyl, aryl, alkyloxy, aryloxy or $NR^5R^6$;

$R^4$ is alkyl, aryl, alkyloxy, aryloxy, alkylthio, arylthio or $NR^5R^6$;

$R^5$ and $R^6$ are the same or different and are hydrogen, alkyl, aryl, $COR^7$ or $SO_2R^7$;

$R^7$ is alkyl, aryl, alkyloxy or aryloxy; n is 1 or 2;

$R^8$ is alkyl, aryl or $NR^9R^{10}$; and $R^9$ and $R^{10}$ are the same or different and are hydrogen, alkyl or aryl;

provided that when Ar is unsubstituted phenyl, $R^1$ and $R^2$ are H, X is NH, Z is

and $X^1$ is O, $R^3$ is not methyl.

In formula (I), halogen includes chloro, bromo, and fluoro and the alkyl and alkoxy groups and moieties each have 1 to 4 carbon atoms. Certain compounds of formula (I) may exist in their solvated forms. The group Ar is formula (I) is preferably unsubstituted or has substituents selected from alkyl (preferably methyl) and/or halogen (preferably chloro) groups.

The term "aryl" as used herein includes phenyl or naphthyl either unsubstituted with one or more substituents, the substituent(s) being the same or different and preferably selected from alkyl, alkoxy, halogen, nitro, cyano and amino.

Preferred compounds of formula (I) include those wherein:
(i) Ar is phenyl or 2,3-dimethylphenyl; and/or
(ii) Z is

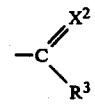

wherein $X^2$ is O or S and $R^3$ is $NR^5R^6$.

A particularly preferred group of compounds of formula (I) are those of formula (Ia)

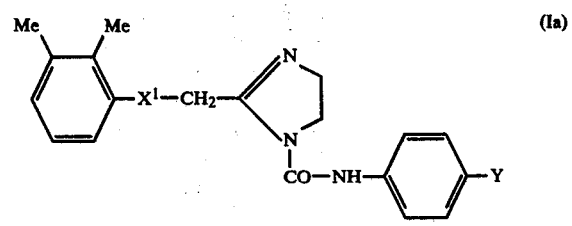

(Ia)

wherein $X^1$ is O or NH; and Y is selected from Cl, Br, F, I, $-NO_2$, $-OR$, $-CN$, $-CO_2R$, $-CONR^1R^2$, $-SO_2NR^1R^2$ and alkyl of from 1 to 4 carbon atoms, in which R is an alkyl group of from 1 to 18 carbon atoms, preferably of from 1 to 4 or of from 12 to 18 carbon atoms; and each of $R^1$ and $R^2$, which may be the same or different, is hydrogen or an alkyl group of from 1 to 18 carbon atoms, preferably of from 1 to 4 carbon atoms or of from 12 to 18 carbon atoms, preferably only one of $R^1$ and $R^2$ being of from 12 to 18 carbon atoms. When $X^1$ in formula (Ia) is O, Y is preferably not selected from Cl, CN or alkyl of from 1 to 4 carbon atoms.

Certain compounds of fromula (I) may exist in their solvated forms.

Particularly preferred compounds of formula (I) are:
1-N-phenylcarbamoyl-2-(2,3-dimethylphenoxymethyl)-2-imidazoline;
1-N-(α-Naphthyl)carbamoyl-2-(2,3-dimethylphenoxymethyl)-2-imidazoline;
1-N-(4-chlorophenyl)carbamoyl-2-(2,3-dimethylphenoxymethyl)-2-imidazoline;
1-N-(4-cyanophenyl)carbamoyl-2-(2,3-dimethylphenoxymethyl)-2-imidazoline; and
1-(N-(4-chlorophenyl)carbamoyl)-2-(2,3-dimethylanilinomethyl)-2-imidazoline.

Other preferred compounds of formula (I) are:
1-(N-(4-methoxyphenyl)carbamoyl)-2-(2,3-dimethylphenoxymethyl)-2-imidazoline;
1-(N-(4-bromophenyl)carbamoyl)-2-(2,3-dimethylphenoxymethyl)-2-imidazoline;
1-(N-(4-nitrophenyl)carbamoyl)-2-(2,3-dimethylphenoxymethyl)-2-imidazoline; and
1-(N-(4-fluorophenyl)carbamoyl)-2-(2,3-dimethylphenoxymethyl)-2-imidazoline.

The compounds of formula (I) and their acid addition salts have activity against Arthropods, in particular against the Order Acarina. The compounds of formula (I) may be used to control pests such as *Rhipicephalus appendiculatus, Boophilus decoloratus, Rhipicephalus evertsi, Amblyomma hebraeum, Psoroptes ovis Boophilus microplus* and *Hyaloma* species on animals and *Tetranychus* species on plants.

The compounds of formula (I) may be prepared by any known method for the preparation of compounds of an analogous structure.

In particular the compounds of formula (I) may be prepared from 2-substituted imidazolines of formula (II) or an acid addition salt thereof;

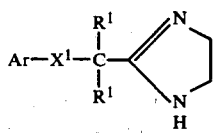
(II)

wherein Ar, $X^1$, $R^1$ and $R^2$ are as defined above, either by a direct addition reaction with an isocyanate or isothiocyanate (to give a compound of formula (I) where Z is an N-substituted carbamoyl or thiocarbamoyl group); a ketene (to give a compound of formula (I) where Z is an acyl group) or a carbodiimide (to give a compound of formula (I) where Z is an amidino group); or by a substitution reaction with a compound of formula (III):

$$Z-X' \qquad (III)$$

where Z is as defined above and X' is a leaving group such as halo (e.g. in acid chlorides or halo-formate esters), acyl (e.g. in acid anhydrides), alkoxy or alkylthio (e.g. carbamates, imidates, thiocarbamates or thiomidates) or sulphonyloxy (e.g. in mixed anhydrides).

In one particular application of the above substitution reaction compounds of formula (I) wherein Z is a thiocarbamoyl group may be prepared by the reaction of a compound of formula (II) with a compound of formula (III) wherein Z is a thiocarbamoyl group and X' is $NH_2$ (i.e. $Z-X'$ is a thiourea).

The reaction may be effected optionally in water or an organic solvent, such as chloroform or methylene chloride, preferably in the presence of a base such as an alkali metal hydroxide, and alkali metal carbonate, or a tertiary organic base, such as triethylamine, pyridine or substituted pyridines or piperidines, e.g. pentamethylpiperidine or tetramethylpiperidine; and generally at temperatures of $-70°$ C. to 120° C., preferably at temperatures of $-10°$ C. to 40° C.

Compounds of formula (I), in particular those wherein Z is not a strong electron withdrawing group, may be prepared by reacting an ethylenediamine of formula (IV) or salt thereof;

$$H_2NCH_2CH_2NH.Z \qquad (IV)$$

wherein Z is as defined hereinabove, with an appropriate phenoxyalkyl or anilinoalkyl carboxylic acid or a reactive derivative thereof such as imidate, thioimidate, imidohalide, ester, amidine, thioamide, nitrile or carboxyalkylthioamide. These reactants may be conveniently represented by formula (V):

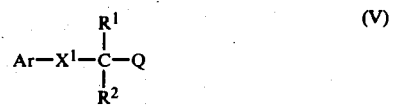

wherein Ar, $X^1$, $R^1$ and $R^2$ are as defined hereinabove and Q is a carboxyl group or a reactive derivative thereof which produces the imidazoline ring structure of formula (I) when reacted with a compound of formula (IV):

Suitable derivatives include:

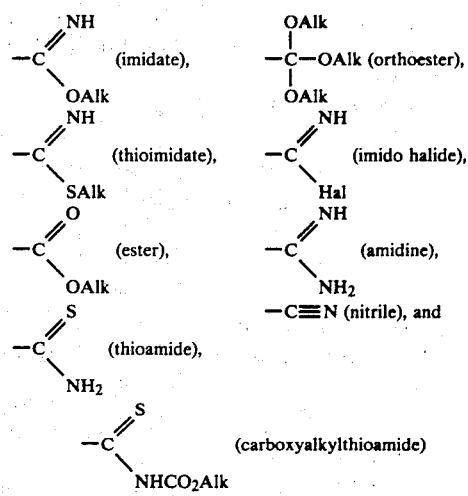

wherein 'Alk' is an alkyl group having 1 to 6 carbon atoms.

The conditions under which this reaction may be carried out of course depend upon the nature of the starting materials used, and a liquid medium may be present or absent; high and low temperatures may be used, and various pressures employed.

When the carboxylic acid derivative is an imidate, this is preferably in the form of an acid addition salt such as a hydrogen halide salt, and may be prepared from the nitrile and a suitable anhydrous alkanol such as ethanol or methanol in the presence of dry diethyl ether or chloroform and hydrogen chloride at a low temperature. The reaction may be carried out at a temperature in the range of $-20°$ C. to ambient temperature. The reaction with an ethylenediamine of formula (IV) is conducted in an inert anhydrous medium such as chloroform, methylene chloride or ether. The reactants are preferably heated under reflux until reaction is complete.

The thiomidate intermediates in the form of acid addition salts may be prepared from the corresponding nitrile by reaction with an alkyl mercaptan and a hydrogen halide gas at low temperatures about 0° C., in the presence of dry diethyl ether. The thioimidate may then be reacted with an ethylenediamine of formula (IV) the reaction being effected at the reflux temperature of the reaction mixture.

The ester intermediates may be conveniently prepared from the corresponding acid by known methods, and the acid itself may be prepared from the corresponding nitrile. They may then be reacted with an ethylenediamine of formula (IV), preferably in the presence of a liquid medium which may be polar or non-polar. The reaction is preferably carried out at an elevated temperature.

The compounds of formula (I) may be prepared from the imidohalide intermediates by reaction with an ethylenediamine of formula (IV), under anhydrous conditions in the presence or absence of an acid acceptor and optionally at an elevated temperature. The reaction mixture may include a polar or non-polar liquid medium such as a lower alkanol or an ether.

The amidine intermediate in the form of the base or acid addition salts thereof, is preferably converted to a compound of formula (I) by heating under reflux with an ethylenediamine of formula (IV) in the presence of a polar or non-polar liquid medium, for example a lower alkanol, until ammonia ceases to be evolved. The amidine intermediates themselves may be prepared by any known method, but conveniently from the corresponding imidates by reaction with ammonia.

The thioamide and amide intermediates may be prepared from the corresponding nitriles or by any other convenient method and may be converted into compounds of formula (I) by heating with an ethylenediamine of formula (IV), at a reflux or higher temperature, in the presence or absence of a polar or non-polar solvent. Conveniently the reactions are partly effected under reduced pressure to induce the removal of ammonia and/or hydrogen sulphide from the reaction mixture.

The nitrile intermediates are reacted in the presence or absence of a liquid medium with an ethylenediamine of formula (IV) or a salt thereof; the reaction may be carried out in the presence of hydrogen sulhide. A liquid medium such as a lower alkanol may be included in the reaction mixture which may be heated to reflux temperature, or to a higher temperature in a closed vessel, optionally in the presence of an inert gas such as nitrogen.

It will of course be understood that where the intermediate is the carboxylic acid, the ester or thioamide, there may be isolated as an intermediate the acylethylenediamines of formula (VI):

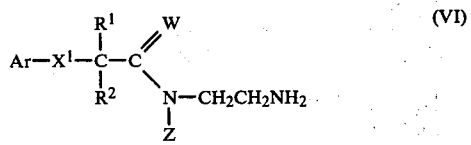
(VI)

wherein Ar, $X^1$, $R^1$, $R^2$ and Z are as defined above and W is oxygen or sulphur and these compounds may themselves be converted in situ to a compound of formula (I), either by separate treatment with a dehydrating agent such as calcium oxide or by continuing the reaction to completion under the original conditions giving rise to a compound of formula (I).

The compounds of formula (I) may be prepared by the reaction of a phenol or amine of formula (VII), or an O- or N-metal compound thereof;

Ar—$X^1$—H     (VII)

wherein Ar and $X^1$ are as defined in formula (I) with a compound of formula (VIII):

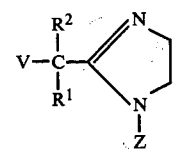
(VIII)

wherein $R^1$, $R^2$ and Z are as defined in formula (I), and V is a leaving group derived from a suitable inorganic or organic acid. Suitable derivatives are halo, such as chloro, iodo, or bromo, alkylsulphonyloxy or arylsulphonyloxy such as p-toluenesulphonyloxy.

The compounds of formula (VIII) may be in the form of their bases or acid addition salts thereof. The reaction is carried out in an inert liquid medium which is preferably a polar liquid such as acetonitrile or isopropanol, or may be dimethylsulphoxide, sulpholane, methyl ethyl ketone, dimethylformamide, acetone, dimethylacetamide, N-methyl-2-pyrrolidone, or mixtures of the foregoing. In the case where V is chloro in a compound of formula (VIII), then a small catalytic quantity of an iodide salt for example sodium iodide, or a phase transfer catalyst such as a quaternary ammonium salt such as benzyltrimethylammonium chloride may advantageously be included in the reaction mixture. The reactants may be heated together under an inert atmosphere such as nitrogen at the reflux temperature of the reaction mixture.

The compounds of formula (I) wherein Z is

and $R^3$ is alkoxy, aryloxy or $NR^5R^6$ may also be prepared by reacting a compound of formula (IX):

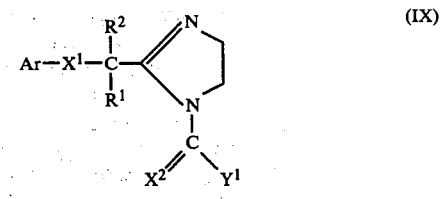
(IX)

in which Ar, $X^1$, $X^2$, $R^1$ and $R^2$ are as defined above and $Y^1$ is a leaving group (such as halo, acyl, alkoxy, alkylthio, S—, SH, sulphonyloxy or carbalkoxy) with a suitable active hydrogen-containing compound of formula (X):

$R^{11}$—H     (X)

wherein $R^1$ is alkoxy, aryloxy or $NR^5R^6$ and $R^5$ and $R^6$ are as defined above.

In one particular aspect this method may be applied to the preparation of compounds of formula (I) in which Z is a carbamoyl group by treatment of compound (IX) in which Y is —SR" and $X^2$ is $NR^4$ where $R^4$ is as defined above and R" is an alkyl group with a suitable active-hydrogen containing compound of formula (X) above. The intermediate compounds of formula (IX) in which Y is SR" and $X^2$ is $NR^4$ may be prepared from compounds of general formula (XI):

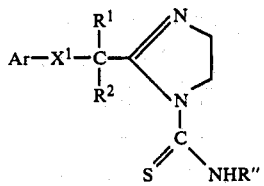

wherein Ar, $X^1$, $R^1$, $R^2$ and R" are as defined above.

The compounds of formula (I), wherein Z is

$R^3$ is as defined above and $X^2$ is $NR^4$ where $R^4$ is as defined in formula (I) above, may also be prepared by reacting a compound of formula (II) above with an imidoyl dihalide of formula (XII):

$$R^4-N=C(Hal)_2 \qquad (XII)$$

where $R^4$ is as defined in formula (I) above and Hal is chloro, bromo or iodo, to give an intermediate of formula (IX) above wherein $X^2$ is $R^4$—N and Y is Hal which may then be converted to a compound of formula (I) by the above described method.

The compounds of formula (I) may be isolated from the reaction mixture as the free base or in the form of an acid addition salt. The bases may be converted into acid addition salts thereof by known techniques with the aid of the appropriate acid, and salts of the compound may also be converted into the free bases or into other acid addition salts.

For use as a pesticide, the compounds of formula (I) may be presented in the form of their free bases, or as acid addition salts thereof. Suitable salts of formula (I) include hydrohalide, sulphate, nitrate, phosphate, thiocyanate, acetate, propionate, stearate, naphthenate, perchlorate, benzoate, methanesulphonate, ethanesulphonate, tosylate and benzenesulphonate acid addition salts thereof.

The compounds of formula (I) may be used as to combat insects, ticks, mites and other arthropods including free living arthropods and those which are ectoparasites of plants, mammals and birds and may be used alone or in combinatiion with an additive which may take the form of one or more of the carriers used in the formulation art, such as: wetting, diluting, stabilising, thickening, emulsifying, dispersing or surface active agents or other standard carrier ingredients.

A formulation may be an aqueous solution of an acid addition salt of a compound of formula (I), or a suspension of a compound of formula (I) in water, and may be used alone or in combination with suitable surface active agents. The formulation per se may be used alone or diluted in water for application to the pests or their immediate environment by way of spraying or dipping.

A formulation may be in the form of a miscible oil comprising a compound of formula (I) in the form of its free base or with equimolar quantity of a suitable organic acid, such as oleic acid or naphthenic acid, to provide a salt soluble in organic solvents, and emulsifiers, and are applied as an emulsion by way of spraying or dipping.

A formulation may be a non-aqueous solution or suspension of a compound of formula (I) in a suitable organic solvent for the direct application by the "pour-on" method. A formulation may also take the form of a wettable powder for dilution with water and application by dipping or spraying. Other solid formulations may also be used for direct application without dilution, such as dusts, powders and granules.

A further formulation may be a paste, grease or gel containing a compound of formula (I) and a suitable carrier, and may be applied by spreading the formulation over the infected area.

An acid addition salt or base of a compound of formula (I) is preferably present in a pesticidal formulation in an amount between 5 and 80%, calculated by weight of the base, and particularly preferred formulations containing about 20%, calculated by weight of the base. The concentration of a compound of formula (I) applied to the pests or their immediate environment may be in the range of 0.001%–20%, calculated by weight of the base.

It will be appreciated from the foregoing that what we will claim may comprise any novel feature described herein, principally and not exclusively, for example:

(a) A novel substituted phenoxyalkyl or anilinoalkyl imidazoline compound of formula (I) and acid addition salts thereof;

(b) A method of preparation of a novel compound of formula (I) and acid addition salts thereof;

(c) A method of controlling arthropod pests, particularly members of the Order Acarina, by applying to the pest or the pest's environment a compound of formula (I);

(d) A pesticidal formulation comprising a compound of formula (I) and a carrier thereof; and (e) A method of making a formulation comprising an admixture of a carrier and a compound of formula (I).

The following Examples are provided by way of an illustration of the present invention and should not be construed as in anyway constituting a limitation thereof.

EXAMPLE 1

Preparation of 2-(2,3-dimethylphenoxymethyl)-1-acetyl-2-imidazoline

A solution of acetic anhydride (3.0 ml; 0.032 moles) in diethyl ether (10 ml) was added dropwise, during 10 minutes, to a stirred suspension of 2-(2,3-dimethylphenoxymethyl)-2-imidazoline (6.12 g; 0.030 mole) (prepared from O-ethyl-2,3-dimethylphenoxyacetimidate and ethylene diamine) in diethyl ether (100 ml) cooling the mixture to keep its temperature below 20° C. After stirring for 2 hours the reaction mixture was filtered and the precipitate recrystallised from acetone to yield white crystals of 2-(2,3-dimethylphenoxymethyl)-1-acetyl-2-imidazoline, m.p. 127°–130° C. Analysis: Calculated C 68.27, H 7.37, N 11.37% Found: C 68.13, H 7.44, N 11.13%.

EXAMPLE 2

2-(2,3-Dimethylphenoxymethyl)-1-N,N-dimethylthiocarbamoyl-2-imidazoline

A solution of dimethylthiocarbamoyl chloride (2.47 g; 0.020 mole) in chloroform (10 ml) was added dropwise during 10 minutes, to a stirred solution of 2-(2,3-dimethylphenoxymethyl)-2-imidazoline (4.08 g; 0.020 mole) prepared as in Example 1—and triethylamine (2.0 g; 0.20 mole) in chloroform (50 ml) cooling to keep the reaction below 5° C. The reaction temperature was then allowed to rise to room temperature and finally the reaction was refluxed for 5 hours. After cooling the reaction mixture was washed with water, dried and evaporated. The residue was recrystallised from isopropanol to yield white crystals of 2-(2,3-dimethylphenoxymethyl)-1-(N,N-dimethylthiocarbamoyl)-2-imidazoline, m.p. 124°-127° C. Analysis: Calculated C 61.84, H 7.27, N 14.42%. Found: C 62.15, H 7.64, N 14.35%.

EXAMPLE 3

2-(2,3-Dimethylphenoxymethyl)-1-(N-methylthiocarbamoyl)-2-imidazoline

A solution of methyl isothiocyanate (1.46 g; 0.20 mole) in chloroform (10 ml) was added dropwise during 10 minutes, to a stirred solution of 2-(2,3-dimethylphenoxymethyl)-2-imidazoline (4.08 g; 0.020 moles) prepared as in Example 1—in chloroform (50 ml) cooling to keep the reaction below 5° C. The reaction mixture was then allowed to warm to room temperature and finally refluxed for 5 hours. Chloroform was then evaporated in vacuo and the residue recrystallised from isopropanol to yield white crystals of 2-(2,3-dimethylphenoxymethyl)-1-N-methylthiocarbamoyl-2-imidazoline, m.p. ca 100° C. with decomposition.

$^1$H-NMR (deuterochloroform—tetramethylsilane internal standard):

| | | | |
|---|---|---|---|
| 8.1-8.3 | ∂ | 1H Broad singlet | |
| 6.8-7.2 | ∂ | 3H Multiplet | |
| 5.0 | ∂ | 2H Singlet | NMR spectra consistent with the proposed structure |
| 3.6-4.5 | ∂ | 4H Multiplet | |
| 3.1 | ∂ | 3H Doublet | |
| 2.2 | ∂ | 6H Doublet | |

EXAMPLE 4

1-N-Phenylcarbamoyl-2-(2,3-dimethylanilinomethyl)-2-imidazoline 2-(2,3-Dimethylanilinemethyl)-2-imidazoline (4.20 g; 0.024 moles) was stirred in methylene chloride (90 ml) cooled to 0° C. and a solution of phenyl isocyanate (2.84 g; 0.024 moles) in methylene chloride (10 ml) was then added dropwise. A white precipitate formed rapidly. Stirring was continued for 2-3 hours after the addition at 0° C., the reaction mixture then allowed to reach ambient temperature and stirring was continued overnight. The reaction mixture was then evaporated to dryness under reduced pressure and the solid residue so obtained recrystallised from propan-2-ol to yield white crystals of 1-N-phenylcarbamoyl-2-(2,3-dimethylanilinomethyl)-2-imidazoline (0.735 H$_2$O) m.p. 137° C.

EXAMPLE 5

1-N-(2,3-Dimethylphenoxycarbonyl)-2-(2,3-dimethylphenoxymethyl)-2-imidazoline 2-(2,3-Dimethylphenoxymethyl)-2-imidazoline (3.0 g; 0.0147 moles) was dissolved in dry chloroform (~40 ml) and cooled to 0° C. Tetramethylpiperidine (2.07 g; 0.0147 moles) in dry chloroform (~7 ml) was then added to the cooled, stirred solution. 2,3-Dimethylphenylchloroformate (2.71 g; 0.0147 moles as a 30% w/v solution in benzene) was slowly added. A white precipitate formed and stirring was continued at 0° C. for 2 hours after which tim the reaction mixture was allowed to rise to ambient temperature. Tetramethylpiperidine hydrochloride was precipitated by the addition of dry acetone and removed by filtration. The filtrate was evaporated to dryness under reduced pressure and the white residue recrystallised from propan-2-ol to give 1-N-(2,3-dimethyl-phenoxycarbonyl)-2-(2,3-dimethylphenoxymethyl)-2-imidazoline, m.p. 126°-127° C.

EXAMPLES 6 TO 27

By methods analogous to those described in Examples 1 to 5 above the compounds of Examples 6 to 27 below are also prepared.

EXAMPLE 6

1-N-Methyloxycarbonyl-2-(2,3-dimethylphenoxymethyl)-2-imidazoline, m.p. 120° C.

EXAMPLE 7

1-N-Methylcarbamoyl-2-(2,3-dimethylphenoxymethyl)-2-imidazoline, m.p. 147°-150° C. (dec.).

EXAMPLE 8

1-N-Phenylthiocarbamoyl-2-(2,3-dimethylphenoxymethyl)-2-imidazoline, m.p. 102°-104° C.

EXAMPLE 9

1-N-4-Toluenesulphonylcarbamoyl-2-(2,3-dimethylphenoxymethyl)-2-imidazoline, m.p. 120° C.

EXAMPLE 10

1-N-(α-Naphthyl)carbamoyl-2-(2,3-dimethylphenoxymethyl)-2-imidazoline, m.p. 156°-158° C.

EXAMPLE 11

1-N-(4-Chlorophenyl)carbamoyl-2-(2,3-dimethylphenoxymethyl)2-imidazoline, m.p. 132° C.

EXAMPLE 12

1-N-(4-Cyanophenyl)carbamoyl-2-(2,3-dimethylphenoxymethyl)-2-imidazoline, m.p. 172°-174° C.

EXAMPLE 13

1-N-Phenylcarbamoyl-2-phenoxymethyl-2-imidazoline, m.p. 170° C.

EXAMPLE 14

1-N,N-Diphenylcarbamoyl-2-(2,3-dimethylphenoxymethyl)-2-imidazoline, m.p. 143°-145° C.

EXAMPLE 15

1-N-p-Tolycarbamoyl-2-(2,3-dimethylphenoxymethyl)-2-imidazoline, m.p. 137° C.

EXAMPLE 16

1-N-Phenylcarbamoyl-2-(α-phenyloxyethyl)-2-imidazoline, m.p. 159° C.

EXAMPLE 17

1-N-(α-Naphthyl)carbamoyl-2-phenoxymethyl-2-imidazoline, m.p. 160°-163° C.

EXAMPLE 18

1-N-Cyclohexylcarbamoyl-2-(2,3-dimethylphenoxymethyl)-2-imidazoline, m.p. 63° C.

EXAMPLE 19

1-N-Phenylcarbamoyl-2-(2-chloroanilinomethyl)-2-imidazoline, m.p. 169° C.

EXAMPLE 20

1-(N-Phenyl-N-methyl)carbamoyl-2-(2,3-dimethylphenoxymethyl)-2-imidazoline, m.p. 112° C.

EXAMPLE 21

1-N-Phenylcarbamoyl-2-(α,α-dimethylphenoxymethyl)-2-imidazoline, m.p. 81°–85° C.

EXAMPLE 22

1-N-Hexadecylcarbamoyl-2-(2,3-dimethylphenoxymethyl)-2-imidazoline, m.p. 76°–77° C.

EXAMPLE 23

1-N-(α-Naphthyl)carbamoyl-2-(3-methylanilinomethyl)-2-imidazoline, m.p. 146° C.

EXAMPLE 24

1-N-Phenylcarbamoyl-2-(2-chloroanilinomethyl)-2-imidazoline, m.p. 168°–169° C.

EXAMPLE 25

1-N-(2,6-Dimethylphenyl)carbamoyl-2-(2,3-dimethylphenoxymethyl)-2-imidazoline perchlorate salt, m.p. 221°–222° C.

EXAMPLE 26

1-N-(2,3-Dichlorophenyl)carbamoyl-2-(2,3-dimethylphenoxymethyl)-2-imidazoline, m.p. 175°–180° C.

EXAMPLE 27

1-N-Phenylcarbamoyl-2-(3-methoxyphenoxymethyl)-2-imidazoline.

EXAMPLE 28

Preparation of 1-methanesulphonyl-2-(2,3-dimethylphenoxymethyl)-2-imidazoline 2-(2,3-Dimethylphenoxymethyl)-2-imidazoline (8.0 g; 0.0392 moles) was dissolved in dry ether (75 ml) and sufficient dry chloroform (50 ml) and the solution cooled in ice (sufficient chloroform was used to prevent precipitation of the imidazoline on cooling). Methanesulphonyl chloride (4.50 g; 0.0393 moles) was added dropwise to the cold, stirred solution. When the addition was complete pentamethylpiperidine (6.08 g; 0.0392 moles) was added and the reaction mixture heated under reflux until tlc showed that reaction was complete (~3 hrs). The reaction mixture was then concentrated under reduced pressure and the residue extracted with a water/chloroform mixture (1:1; ~100 ml). The chloroform layer was washed with water, dried over magnesium sulphate and evaporated under reduced pressure to give a residue which was recrystallised from isopropanol to give 1-methanesulphonyl-2-(2,3-dimethylphenoxymethyl)-2-imidazoline, m.p. 142°–143° C.

EXAMPLE 29

By a method analogous to that used in Example 28 1-benzenesulphonyl-2-(2,3-dimethylphenoxymethyl)-2-imidazoline, m.p. 108°–110° C., was prepared.

EXAMPLE 30

Preparation of 1-N-phenylcarbamoyl-2-(2,3-dimethylphenoxymethyl)-2-imidazoline (A) A solution of 2-(2,3-dimethylphenoxymethyl)-2-imidazoline (20.4 g; 1.0 moles) in methylene chloride (300 ml) was cooled to −65° C. and a solution of phenylisocyanate (11.9 g; 1.0 moles) in methylene chloride (300 ml) added dropwise during 30 minutes. The reaction mixture was then allowed to warm to ambient temperature and left to stand for 2 hours, when a precipitate had formed. The reaction mixture was evaporated under reduced pressure and the residue recrystallised from acetone to give 1-N-phenylcarbamoyl-2-(2,3-dimethylphenoxymethyl)-2-imidazoline, m.p. 150°–152° C.

B. via the N-Chlorocarbamoyl adduct of 2-(2,3-dimethylphenoxymethyl)-2-imidazoline A 17% solution of phosgene in toluene (3.2 g containing 0.5521 g., 0.00549 moles $COCl_2$) in dry chloroform (15 ml) was added slowly with stirring at 0° C. to a solution of 2-(2,3-dimethylphenoxymethyl)-2-imidazoline (2.40 g, 0.0115 moles) in dry chloroform (20 ml). When addition was complete the reaction mixture was left at ambient temperature for 2 hours, diluted with an equal volume of dry diethylether and rapidly filtered. The filtrate, which contained the N-chlorocarbamoyl adduct of 2-(2,3-dimethylphenoxymethyl)-2-imidazoline, was treated with freshly distilled dry aniline (0.664 g, 0.00714 moles) and the mixture left at ambient temperature overnight at which time tlc showed that the major compound was the desired product. The mixture was evaporated to dryness in vacuo and the residue taken up in a mixture of aqueous sodium carbonate and dichloromethane. The organic layer was washed with water, dried over magnesium sulphate and evaporated to dryness to give a residue which was purified as described in (A) above to give 1-N-phenylcarbamoyl-2-(2,3-dimethylphenoxymethyl)-2-imidazoline, identical with that obtained in (A) above.

EXAMPLE 31

Engorged female ticks of the Biarra Strain of *Boophilus microplus* are immersed, in groups of 20 ticks, per concentration in a range of dilutions of the compound under test. The wash is prepared immediately prior to the test by dilution (with water) of the compound under test. The constituents may be in the form of miscible oil or wettable powder formulations. The desired range of concentrations for the test is obtained by further dilution of the master solution or wash.

The ticks are removed from the wash after 10 minutes, dried, and stuck dorsal down on double-sided adhesive tape. They remain in this position for 14 days when the numbers laying viable eggs are determined. From this data a regression line is plotted (concentration against % inhibition of egg-production) and the IR90 and IR99 (concentrations at which 90% and 99% inhibition respectively of egg-production occurs).

The results obtained are shown in Table 1 below.

TABLE 1

| Compound | Example No. | IR90 | IR99 |
|---|---|---|---|
| 1-N-Phenylcarbamoyl-2-(2,3-dimethylphenoxymethyl)-2-imidazoline | 30 | <0.016% | — |
| 1-N-(α-Naphthyl)carbamoyl-2-(2,3-dimethylphenoxymethyl)-2-imidazoline | 10 | 0.0032% | 0.0054% |
| 1-N-Phenylcarbamoyl-2-phenoxymethyl-2-imidazoline | 13 | <0.2% | — |

EXAMPLE 32

Test compounds were formulated in polyethyleneglycol and injected into ticks at a site just ventral to the mouth parts. After 14 days the percentage inhibition of egg production (IR) was determined. The results are shown in Table 2 below.

TABLE 2

| Compound | Example No. | % IR |
|---|---|---|
| 1-N-Phenylcarbamoyl-2-(2,3-dimethylphenoxymethyl)-2-imidazoline | 30 | 40% at 0.1mg/ml<br>70% at 1.0mg/ml |
| 1-N-phenylcarbamoyl-2-phenoxymethyl-2-imidazoline | 13 | 100% at 10mg/ml |
| 1-N-Phenylcarbamoyl-2-(2,3-dimethylanilinomethyl)-2-imidazoline | 4 | 50% at 0.1mg/ml |
| 1-N-(α-Naphthyl)carbamoyl-2-(2,3-dimethylphenoxymethyl)-2-imidazoline | 10 | 40% at 0.1mg/ml |
| 1-N,N-Diphenylcarbamoyl-2-(2,3-dimethylphenoxymethyl)-2-imidazoline | 14 | 70% at 1.0mg/ml |
| 1-N-(4-Chlorophenyl)carbamoyl-2-(2,3-dimethylphenoxymethyl)-2-imidazoline | 11 | 70% at 0.1mg/ml |
| 1-N-(4-Toluenesulphonyl)carbamoyl-2-(2,3-dimethylphenoxymethyl)-2-imidazoline | 9 | 100% at 1.0mg/ml |
| 1-N-(4-Tolyl)carbamoyl-2-(2,3-dimethylphenoxymethyl)-2-imidazoline | 15 | 40% at 0.1mg/ml<br>90% at 1.0mg/ml |
| 1-N-Methylcarbamoyl-2-(2,3-dimethylphenoxymethyl)-2-imidazoline | 7 | 80% at 1.0mg/ml |
| 1-N-(α-Naphthyl)carbamoyl-2-phenoxymethyl-2-imidazoline | 17 | 70% at 1.0mg/ml |

EXAMPLE 33

1-(N-(4-Chlorophenyl)carbamoyl)-2-(2,3-dimethylanilinomethyl)-2-imidazoline 2-(2,3-Dimethylanilinomethyl)-2-imidazoline (4.20 g; 0.024 moles) was stirred in methylene chloride (90 ml), cooled to 0° C. and a solution of 4-chlorophenyl isocyanate (3.66 g; 0.024 moles) in methylene chloride (10 ml) was then added dropwise. A white precipitate formed rapidly. Stirring was continued for 2 to 3 hours after the addition at 0° C., the reaction mixture then allowed to reach ambient temperature and stirring was continued overnight. The reaction mixture was then evaporated to dryness under reduced pressure and the solid residue so obtained recrystallised from propan-2-ol to yield white crystals of 1-(N-(4-chlorophenyl)-carbamoyl)-2-(2,3-dimethylanilinomethyl)-2-imidazoline m.p. 153°–155° C.

EXAMPLES 34 TO 37

By methods analogous to that described in Example 33 above the compounds of Examples 34 to 37 below were also prepared.

EXAMPLE 34

1-(N-(4-Methoxyphenyl)carbamoyl)-2-(2,3-dimethylphenoxymethyl)-2-imidazoline, m.p. 126°–127° C. (white powder).

EXAMPLE 35

1-(N-(4-Nitrophenyl)carbamoyl)-2-(2,3-dimethylphenoxymethyl)-2-imidazoline, monohydrate, m.p. 182°–185° C. (pale yellow powder).

EXAMPLE 36

1-(N-(4-Carbethoxyphenyl)carbamoyl)-2-(2,3-dimethylphenoxymethyl)-2-imidazoline, m.p. 153° C. (white powder).

EXAMPLE 37

1-(N-(4-Fluorophenyl)carbamoyl-2-(2,3-dimethylphenoxymethyl)-2-imidazoline, m.p. (about 5% impurity) 172°–173° C.

EXAMPLE 38

Preparation of 1-(N-(4-Bromophenyl)carbamoyl)-2-(2,3-dimethylphenoxymethyl)-2-imidazoline A. A solution of 2-(2,3-dimethylphenoxymethyl)-2-imidazoline (20.4 g; 1.0 mol) in methylene chloride (300 ml) was cooled to −65° C. and a solution of 4-bromophenylisocyanate (19.8 g; 1.0 mol) in methylene chloride (300 ml) added dropwise during 30 minutes. The reaction mixture was then allowed to warm to ambient temperature and left to stand for 2 hours, when a precipitate had formed. The reaction mixture was evaporated under reduced pressure and the residue recrystallised from acetone to give 1-(N-(4-bromophenyl)-carbamoyl)-2-(2,3-dimethylphenoxymethyl)-2-imidazoline monohydrate, m.p. 150°–151° C.

B. via the N-Chlorocarbamoyl adduct of 2-(2,3-dimethylphenoxymethyl)-2-imidazoline A 17% solution of phosgene in toluene (3.2 g containing 0.5521 g; 0.00549 moles COCl₂) in dry chloroform (15 ml) was added slowly with stirring at 0° C. to a solution of 2-(2,3-dimethylphenoxymethyl)-2-imidazoline (2.40 g, 0.0115 moles) in dry chloroform (20 ml). When addition was complete the reaction mixture was left at ambient temperature for 2 hours, diluted with an equal volume of dry diethylether and rapidly filtered. The filtrate, which contained the N-chlorocarbamoyl adduct of 2-(2,3-dimethylphenoxymethyl)-2-imidazoline, was treated with freshly distilled dry 4-bromoaniline (1.22 g, 0.00714 moles) and the mixture left at ambient temperature overnight at which time tlc showed that the major compound was the desired product. The mixture was evaporated to dryness in vacuo and the residue taken up in a mixture of aqueous sodium carbonate and dichloromethane. The organic layer was washed with water, dried over magnesium sulphate and evaporated to dryness to give a residue which was purified as described in (A) above to give 1-(N-(4-bromophenyl)carbamoyl-2-(2,3-dimethylphenoxymethyl)-2-imidazoline, identical with that obtained in (A) above.

EXAMPLE 39

Engorged female ticks of the Biarra Strain of *Boophilus microplus* are immersed, in groups of 20 ticks, per concentration in washes of a range of dilutions of the compound under test. The wash is prepared immediately prior to the test by dilution (with water) of the compound under test. The constituents may be in the form of miscible oil or wettable powder formulations. The desired range of concentrations for the test is obtained by further dilution of the master solution or wash.

The ticks are removed from the wash after 10 minutes, dried, and stuck dorsal side down on double-sided adhesive tape. They remain in this position for 14 days when the numbers laying viable eggs are determined. From this data a regression line is plotted (concentration against % inhibition of egg-production) and the IR99 (concentration at which 99% inhibition of egg-production occurs) is derived.

The results obtained are shown in Table 1 below.

TABLE 1

| Compound | Example No. | IR99 |
|---|---|---|
| 1-(N-(4-Bromophenylcarbamoyl)-2-(2,3-dimethylphenoxymethyl)-2-imidazoline | 2 | 0.0095% |
| 1-(N-(4-Methoxyphenyl)carbamoyl)-2-(2,3-dimethylphenoxymethyl)-2-imidazoline | 3 | 0.0038% |
| 1-(N-(4-Nitrophenyl)carbamoyl)-2-(2,3-dimethylphenoxymethyl)-2-imidazoline hydrate | 4 | 0.010% |
| 1-(N-(4-Carbethoxyphenyl)carbamoyl)-2-(2,3-dimethylphenoxymethyl)-2-imidazoline. | 5 | 0.019% |

The following formulations are given to illustrate the way in which the pesticidal compounds of the invention can be applied to pests or environments susceptible to pest attack.

FORMULATION 1
Dusting Powders

| Active Compound | 1.0 | 20.0 parts by wt. |
|---|---|---|
| Talc | 99.0 | 80.0 parts by wt. |
| | 100.0 | 100.0 |

FORMULATION 2
Wettable Powder

| Active Compound | 25.0 parts by wt. |
|---|---|
| Sodium Dioctyl Sulphosuccinate | 1.0 parts by wt. |
| Dispersol ACA | 2.0 parts by wt. |
| Kaolin | 72.0 parts by wt. |
| | 100.0 |

FORMULATION 3
Aqueous Dispersion

| Active Compound | 20.0 parts by wt. |
|---|---|
| Keltrol | 0.4 parts by wt. |
| Sodium Dioctyl Sulphosuccinate | 0.5 parts by wt. |
| Water | 79.1 parts by wt. |
| | 100.0 |

FORMULATION 4
Pour-On

| Active Compound | 5.0 parts by wt. |
|---|---|
| Dimethyl Formamide | 85.0 parts by wt. |
| Castor Oil | 10.0 parts by wt. |
| | 100.0 |

FORMULATION 5
Grease

| Active Compound | 6.0 parts by wt. |
|---|---|
| Petroleum Jelly | 94.0 parts by wt. |
| | 100.0 |

FORMULATION 6
Miscible Oil

| Compound from Example 22 | 10.0 parts by wt. |
|---|---|
| Aromasol H | 70.0 parts by wt. |
| Nonyl Phenol Ethoxylate | 20.0 parts by wt. |
| | 100.0 |

What is claimed is:
1. A compound of formula (I)

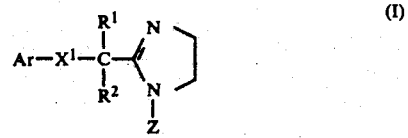

wherein Ar is unsubstituted or mono-, di or tri-substituted phenyl in which the substituents are the same or different and are selected from $C_{1-4}$ alkyl, $C_{1-4}$ alkoxy, halogen, hydroxy, cyano, amino, trifluoromethyl or nitro and in which any two adjacent carbon atoms on the phenyl ring may optionally be joined by a carbon chain having 3 or 4 carbon atoms;

$X^1$ is O or NH;

$R^1$ and $R^2$ are the same or different and are hydrogen or $C_{1-4}$ alkyl;

Z is a group

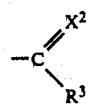

in which $X^2$ is O or S;

and $R^3$ is $C_{1-4}$ alkyloxy, aryloxy or $NR^5R^6$, where "aryl" is phenyl or naphthyl either unsubstituted or substituted with one or more substituent(s) which are the same or different and which are selected from $C_{1-4}$ alkyl, $C_{1-4}$ alkoxy, halogen, nitro, cyano and amino; and $R^5$ and $R^6$ are the same or different and are hydrogen, $C_{1-4}$ alkyl or aryl where "aryl" is as defined with respect to $R^3$; or an acid addition salt thereof.

2. A compound according to claim 1 wherein Ar is selected from the group consisting of unsubstituted phenyl and substituted phenyl having one or more substituents which are the same or different and are $C_{1-4}$ alkyl or halogen.

3. A compound according to claim 1 wherein Ar is substituted phenyl having one or more substituents which are the same or different and are $C_{1-4}$ alkyl or halogen.

4. A compound according to claim 3 in which Ar is substituted phenyl wherein the substituent(s) are selected from methyl and chloro.

5. A compound according to claim 1 wherein Ar is disubstituted phenyl.

6. A compound according to claim 1 wherein Ar is 2,3-dimethylphenyl.

7. A compound according to claim 1 wherein $X^2$ is O and $R^3$ is $NR^5R^6$ where $R^5$ and $R^6$ are as defined in claim 1.

8. A compound according to claim 1 wherein $X^2$ is S and $R^3$ is $NR^5R^6$ where $R^5$ and $R^6$ are as defined in claim 1.

9. A compound according to claim 7 wherein $R^5$ is hydrogen and $R^6$ is aryl.

10. A compound according to claim 8 wherein $R^5$ is hydrogen and $R^6$ is aryl.

11. A compound according to claim 7 wherein Ar is selected from the group consisting of unsubstituted phenyl and substituted phenyl having one or more substituents which are the same or different and are $C_{1-4}$ alkyl or halogen.

12. A compound according to claim 7 wherein Ar is substituted phenyl having one or more substituents which are the same or different and are $C_{1-4}$ alkyl or halogen.

13. A compound according to claim 7 in which Ar is substituted phenyl wherein the substituent(s) are selected from methyl and chloro.

14. A compound according to claim 7 wherein Ar is disubstituted phenyl.

15. A compound according to claim 7 wherein Ar is 2,3-dimethylphenyl.

16. A compound according to claim 9 wherein Ar is selected from the group consisting of unsubstituted phenyl and substituted phenyl having one or more substituents which are the same or different and are $C_{1-4}$ alkyl or halogen.

17. A compound according to claim 9 wherein Ar is substituted phenyl having one or more substituents which are the same or different and are $C_{1-4}$ alkyl or halogen.

18. A compound according to claim 9 in which Ar is substituted phenyl wherein the substituent(s) are selected from methyl and chloro.

19. A compound according to claim 9 wherein Ar is disubstituted phenyl.

20. A compound according to claim 9 wherein Ar is 2,3-dimethylphenyl.

21. A compound according to claim 9 wherein $R^6$ is selected from the group consisting of phenyl, 4-chlorophenyl, 4-cyanophenyl and α-naphthyl.

22. A compound according to claim 16 wherein $R^6$ is selected from the group consisting of phenyl, 4-chlorophenyl, 4-cyanophenyl and α-naphthyl.

23. A compound according to claim 18 wherein $R^6$ is selected from the group consisting of phenyl, 4-chlorophenyl, 4-cyanophenyl and α-naphthyl.

24. A compound according to claim 19 wherein $R^6$ is selected from the group consisting of phenyl, 4-chlorophenyl, 4-cyanophenyl and α-naphthyl.

25. A compound according to claim 20 wherein $R^6$ is selected from the group consisting of phenyl, 4-chlorophenyl, 4-cyanophenyl and α-naphthyl.

26. 1-(N-Phenylcarbamoyl)-2-(2,3-dimethylphenoxymethyl)-2-imidazoline or an acid addition salt thereof.

27. 1-[N-(α-Naphthyl)carbamoyl]-2-(2,3-dimethylphenoxymethyl)-2-imidazoline or an acid addition salt thereof.

28. 1-[N-(4-Chlorophenyl)carbamoyl]-2-(2,3-dimethylphenoxymethyl)-2-imidazoline or an acid addition salt thereof.

29. 1-[N-(4-Cyanophenyl)carbamoyl]-2-(2,3-dimethylphenoxymethyl)-2-imidazoline or an acid addition salt thereof.

30. An arthropodicidal formulation comprising, as active ingredient, an arthropodicidally effective amount of a compound of formula (I) as defined in claim 1 or an acid addition salt thereof together with a carrier therefor.

31. A formulation according to claim 30 wherein the active ingredient is present in an amount of from 5 to 80% calculated by weight of the base.

32. A formulation according to claim 31 wherein the active ingredient is present in an amount of about 20% calculated by weight of the base.

33. A formulation according to claim 30 in the form of a wettable powder.

34. A formulation according to claim 30 wherein the active ingredient is 1-(N-phenylcarbamoyl)-2-(2,3-dimethylphenoxymethyl)-2-imidazoline or an acid addition salt thereof.

35. A formulation according to claim 30 wherein the active ingredient is 1-[N-(α-naphthyl)carbamoyl]-2-(2,3-dimethylphenoxymethyl)-2-imidazoline or an acid addition salt thereof.

36. A formulation according to claim 30 wherein the active ingredient is 1-[N-(4-chlorophenyl)carbamoyl]-2-(2,3-dimethylphenoxymethyl)-2-imidazoline or an acid addition salt thereof.

37. A formulation according to claim 30 wherein the active ingredient is 1-[N-(4-cyanophenyl)carbamoyl]-2-(2,3-dimethylphenoxymethyl)-2-imidazoline or an acid addition salt thereof.

38. A method of controlling arthropod pests which comprises applying to the pest or the pest's environment an arthropodicidally effective amount of a compound of formula (I) as defined in claim 1 or an acid addition salt thereof.

39. A method according to claim 38 wherein the compound is applied at a concentration of 0.001% to 20%, calculated by weight of the base.

40. A method according to claim 38 wherein the pest is a member of the order Acarina.

41. A method according to claim 40 wherein the compound is 1-[N-(4-chlorophenyl)carbamoyl]-2-(2,3-dimethylphenoxymethyl)-2-imidazoline or an acid addition salt thereof.

42. A compound of formula (Ia)

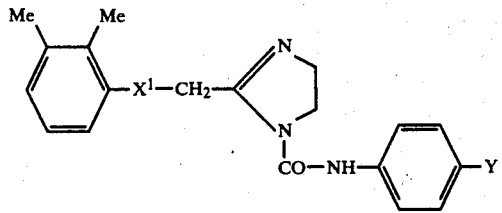

(Ia)

wherein $X^1$ is O or NH; and Y is selected from Cl, Br, F, I, —$NO_2$, —OR, —CN, —$CO_2R$, —$CONR^1R^2$, and alkyl of from 1 to 4 carbon atoms, in which R is an alkyl group of from 1 to 18 carbon atoms; and each of $R^1$ and $R^2$, which may be the same or different, is hydrogen or an alkyl group of from 1 to 18 carbon atoms; or an acid addition salt thereof.

43. A compound according to claim 42 wherein $X^1$ is O and Y is selected from Br, F, I, $NO_2$, OR, $CO_2R$ or $CONR^1R^2$ where R, $R^1$ and $R^2$ are as defined in claim 42.

44. A compound according to claim 42 wherein $X^1$ is NH.

45. 1-[N-(4-chlorophenyl)carbamoyl]-2-(2,3-dimethylanilinomethyl)-2-imidazoline or an acid addition salt thereof.

46. 1-[N-(4-methoxyphenyl)carbamoyl]-2-(2,3-dimethylphenoxymethyl)-2-imidazoline or an acid addition salt thereof.

47. 1-[N-(4-bromophenyl)carbamoyl]-2-(2,3-dimethylphenoxymethyl)-2-imidazoline or an acid addition thereof.

48. 1-[N-(4-nitrophenyl)carbamoyl]-2-(2,3-dimethylphenoxymethyl)-2-imidazoline or an acid addition salt thereof.

49. 1-[N-(4-fluorophenyl)carbamoyl]-2-(2,3-dimethylphenoxymethyl)-2-imidazoline or an acid addition salt thereof.

50. An arthropodicidal formulation comprising as active ingredient an arthropodically effective amount of a compound of formula (Ia) as defined in claim 42 or an acid addition salt thereof together with a carrier therefor.

51. A formulation according to claim 50 wherein the active ingredient is present in an amount from 5 to 80% calculated by weight of the base.

52. A formulation according to claim 50 wherein the active ingredient is 1-[N-(4-chlorophenyl)carbamoyl]-2-(2,3-dimethylanilinomethyl)-2-imidazoline or an acid addition salt thereof.

53. A formulation according to claim 50 wherein the active ingredient is 1-[N-(4-methoxyphenyl)carbamoyl]-2-(2,3-dimethylphenoxymethyl)-2-imidazoline or an acid addition thereof.

54. A formulation according to claim 50 wherein the active ingredient is 1-[N-(4-bromophenyl)carbamoyl]-2-(2,3-dimethylphenoxymethyl)-imidazoline or an acid addition salt thereof.

55. A formulation according to claim 50 wherein the active ingredient is 1-[N-(4-nitrophenyl)carbamoyl]-2-(2,3-dimethylphenoxymethyl)-2-imidazoline or an acid addition thereof.

56. A formulation according to claim 50 wherein the active ingredient is 1-[N-(4-fluorophenyl)carbamoyl]-2-(2,3-dimethylphenoxymethyl)-2-imidazoline or an acid addition salt thereof.

57. A method of controlling arthropod pests which comprises applying to the pest or the pest's environment an arthropodicidally effective amount of a compound of formula (Ia) as defined in claim 42 or an acid addition salt thereof.

58. A method according to claim 57 wherein the compound is applied at a concentration of 0.001% to 20% calculated by weight of the base.

59. A method according to claim 57 wherein the pest is a member of the order Acarina.

60. A method according to claim 59 wherein the compound is 1-[N-(4-chlorophenyl)carbamoyl]-2-(2,3-dimethylanilinomethyl)-2-imidazoline or an acid addition salt thereof.

* * * * *